United States Patent
Vigsnæs et al.

(10) Patent No.: US 11,541,067 B2
(45) Date of Patent: *Jan. 3, 2023

(54) HMO COMPOSITIONS AND METHODS FOR REDUCING DETRIMENTAL PROTEOLYTIC METABOLITES

(71) Applicant: Glycom A/S, Hørsholm (DK)

(72) Inventors: Louise Kristine Vigsnæs, Copenhagen (DK); Bruce McConnell, La Tour de Peilz (CH)

(73) Assignee: Glycom A/S, Hørsholm (DK)

(*) Notice: Subject to any disclaimer, the term of this patent is extended or adjusted under 35 U.S.C. 154(b) by 388 days.

This patent is subject to a terminal disclaimer.

(21) Appl. No.: 16/616,338

(22) PCT Filed: May 24, 2018

(86) PCT No.: PCT/IB2018/053675
§ 371 (c)(1),
(2) Date: Nov. 22, 2019

(87) PCT Pub. No.: WO2018/215960
PCT Pub. Date: Nov. 29, 2018

(65) Prior Publication Data
US 2020/0155580 A1    May 21, 2020

(30) Foreign Application Priority Data
May 24, 2017    (DK) .......................... PA 2017 70378

(51) Int. Cl.
*A61K 31/702*    (2006.01)
*A61K 9/00*    (2006.01)
*A61P 1/00*    (2006.01)

(52) U.S. Cl.
CPC .......... *A61K 31/702* (2013.01); *A61K 9/0053* (2013.01); *A61P 1/00* (2018.01)

(58) Field of Classification Search
CPC ................ A61K 31/702; A61K 9/0053; A61K 2300/00; A61P 1/16; A61P 25/00; A61P 25/22; A61P 25/24; A61P 1/00; A61P 35/00; A23L 33/125
USPC .......................................................... 514/54
See application file for complete search history.

(56) References Cited

U.S. PATENT DOCUMENTS

| | | | |
|---|---|---|---|
| 2009/0098240 A1 | 4/2009 | Mills et al. | |
| 2012/0172319 A1* | 7/2012 | Chow ..................... | A23L 33/12 514/54 |
| 2012/0294840 A1* | 11/2012 | Newburg ............. | A61K 31/702 536/123 |
| 2015/0290260 A1 | 10/2015 | Chichlowski et al. | |
| 2016/0287637 A1* | 10/2016 | McConnell ............ | A61K 35/20 |

FOREIGN PATENT DOCUMENTS

| | | |
|---|---|---|
| EP | 1157697 A1 | 11/2001 |
| WO | 01/04341 A1 | 1/2001 |
| WO | 2007101862 A1 | 9/2007 |
| WO | 2008111832 A1 | 9/2008 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012007588 A9 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013025104 A1 | 2/2013 |
| WO | 2013032674 A1 | 3/2013 |
| WO | WO 2013/032674 A1 * | 3/2013 ........... A61K 31/702 |
| WO | 2013044928 A1 | 4/2013 |
| WO | 2013091660 A1 | 6/2013 |
| WO | 2013139344 A1 | 9/2013 |
| WO | 2014100126 A1 | 6/2014 |
| WO | 2014187464 A1 | 11/2014 |
| WO | 2016014473 A2 | 1/2016 |
| WO | 2016138911 A1 | 9/2016 |
| WO | 2017071716 A1 | 5/2017 |

OTHER PUBLICATIONS

Pieper et al, Animal Health Research Reviews, 2016, 17(2), 137-147.*
Wang et al., Dig Dis Sci, 2012, 57, 2096-2102.*
18805762.4, "Extended European Search Report", EPO, dated Sep. 29, 2020, pp. 1-8.
M. Chichlowski, et al., "Bifidobacteria isolated from infants and cultured on human milk oligosaccharides affect intestinal epithelial function", J Pediatr Gastroenterol Nutr., Sep. 2012, pp. 1-17.
F. Bottacini, et al., "Diversity, ecology and intestinal function of bifidobacteria", 11th International Symposium on Lactic Acid Bacteria Egmond aan Zee, the Netherlands, Aug. 31-Sep. 4, 2014, pp. 1-15.
A. Kindworth et al., Evaluation of general 16S ribosomal RNA gene PCR primers for classical and next-generation sequencing-based diversity studies, Nucleic Acids Research, 2013, vol. 41, No. 1, Aug. 28, 2012, pp. 1-11.

(Continued)

*Primary Examiner* — Ganapathy Krishnan
(74) *Attorney, Agent, or Firm* — Kunzler Bean & Adamson; Tom Briscoe

(57) ABSTRACT

A method and a composition comprising human milk oligosaccharides for decreasing the production of detrimental proteolytic metabolites such as ammonia and branched chain fatty acids in the intestinal microbiota of humans, which is useful for the treatment of brain-gut disorders like autism, stress, anxiety, and depressive disorders, are disclosed. Methods of treatment of colon cancer and liver damage are also disclosed.

18 Claims, 1 Drawing Sheet

(56) References Cited

OTHER PUBLICATIONS

S. Duranti et al., "Exploration of the Genomic Diversity and Core Genome of the Bifidobacterium adolescentis Phylogenetic Group by Means of a Polyphasic Approach", Applied and Environmental Microbiology vol. 79 No. 1, Jan. 2013, pp. 336-346.

Xi Chen, "Human Milk Oligosaccharides (HMOS): Structure, Function, and Enzyme-Catalyzed Synthesis" Advances in Carbohydrate Chemistry and Biochemistry, vol. 72, 2015, pp. 113-190.

L. Bode, "Human milk oligosaccharides and their beneficial effects", Handbook of dietary and nutritional aspects of human breast milk, Human Health Handbooks No. 5, 2013, pp. 515-531.

T. Urashima et al., "Milk Oligosaccharides", Nova Biomedial Books, 2011, pp. 1-99.

RC Edgar, "UPARSE: highly accurate OTU sequences from microbial amplicon reads", Nature Methods vol. 10 No. 10, Oct. 2013, pp. 996-1000.

C. Villodre et al., "Down-regulation of monocarboxylate transporter 1 (MCT1) gene expression in the colon of piglets is linked to bacterial protein fermentation and pro-inflammatory cytokine-mediated signalling", British Journal of Nutrition (2015), 113, Feb. 6, 2015, pp. 610-617.

L. Wang et al., "Elevated Fecal Short Chain Fatty Acid and Ammonia Concentrations in Children with Autism Spectrum Disorder", Dig Dis Sci, Springer, Apr. 3, 2012, pp. 1-7.

"Information From European Union Institutions, Bodies, Offices and Agencies European Commission", Official Journal of the European Union, Nov. 25, 2017, pp. 1-15.

CL Vernazzaa et al., "Human Colonic Microbiology and the Role of Dietary Intervention: Introduction to Prebiotics", Prebiotics: Development and Application, 2006, pp. 1-28.

R. Pieper, Health relevance of intestinal protein fermentation in young pigs, Animal Health Research Reviews 17(2);, Aug. 30, 2016, pp. 137-147.

A. Burokas et al., "Targeting the Microbiota-Gut-Brain Axis: Prebiotics have Anxiolytic and Antidepressant-like Effects and Reverse the Impact of Chronic Stress in Mice", Biological Psychiatry, Oct. 1, 2017, pp. 472-487.

AJ Tarr, "The prebiotics 3'Sialyllactose and 6'Sialyllactose diminish stressor-induced anxiety-like behavior and colonic microbiota alterations: Evidence for effects on the gut-brain axis", Brain, Behavior, and Immunity, Contents lists available at ScienceDirect, Jun. 30, 2015, pp. 1-12.

Monique Haarman et al., "Quantitative Real-Time PCR Assays to Identify and Quantify Fecal *Bifidobacterium* Species in Infants Receiving a Prebiotic Infant Formula", Biomedical Research Department, Microbiology Section, Numico Research BV, 2004 vol. 71, No. 5, Nov. 30, 2004, pp. 1-7.

* cited by examiner

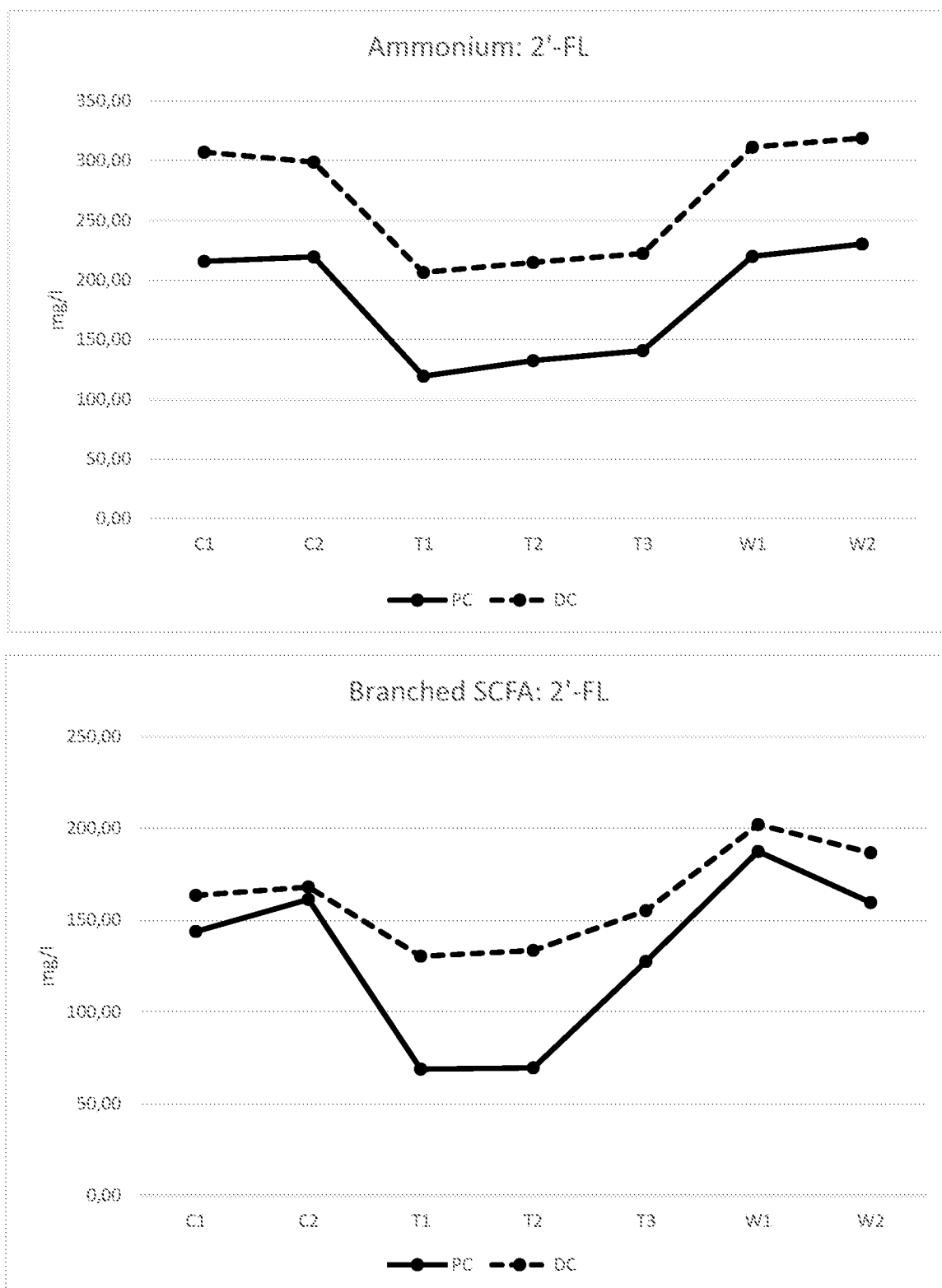

HMO COMPOSITIONS AND METHODS FOR REDUCING DETRIMENTAL PROTEOLYTIC METABOLITES

FIELD OF THE INVENTION

This invention relates to a method and composition for decreasing the production of detrimental proteolytic metabolites such as ammonia and branched chain fatty acids in the intestinal microbiota of humans.

BACKGROUND OF THE INVENTION

It has been estimated that the human intestine harbours $10^{13}$ to $10^{14}$ bacterial cells and the number of bacteria outnumbers the total number of cells in the body by a factor of 10. The microbiota of the human intestine is a complex and very dynamic microbial ecosystem, which is considered to serve numerous important functions for its human host, including protection against pathogens, induction of immune regulatory functions, nutrient processing and metabolic functions. The intestinal microbiota consists of various populations, which are important to preserve human health, and recent research has been able to link imbalances in the intestinal bacterial population to both intestinal and extra-intestinal inflammatory diseases.

In the large intestine, non-digested dietary compounds as well as secreted endogenous substrates can be fermented by the indigenous bacteria, and the substrate availability is a major driver for bacterial fermentation pathways. Hence, metabolites formed by the gut microbiota are largely determined by the composition of the diet and the pattern of food intake, and it is now clear that the species composition of the colonic microbiota is itself altered by the diet.

Non-digestible carbohydrates that reach the large intestine are used by the indigenous saccharolytic bacteria, which results in production of metabolites such as short-chain fatty acids (SCFAs); mainly acetate, propionate and butyrate. SCFAs exert multiple beneficial effects on human health. Acetate can enhance intestinal defence mediated by epithelial cells and thereby protect the host against assault. Butyrate is mainly metabolised by epithelial cells and has been proposed as the main energy source for colonocytes, and has been reported to regulate the physical and functional integrity of the normal colonic mucosa by altering mucin gene and tight junction expression.

Proteins that enter the large intestine non-digested, promote putrefactive fermentation and selective growth of proteolytic bacteria such as members of *Fusobacteria, Streptococcaceae, Megasphera, Selenomonas, Bacteroidetes* and *Proteobacteria* but also putatively pathogenic species such as *E. coli, Klebsiella* spp., *Campylobacter* spp., *Streptococcus* spp., *C. perfringens* and *C. difficile*. When proteins are utilized by these bacteria, branched short chain fatty acids (B-SOFA), ammonia, amines and phenolic compounds are produced, some of which are potentially harmful to human health (Pieper et al. *Anim. Health Res.* Rev. 17, 137 (2016).

Ammonia can interfere with the oxidative metabolism of SOFA in colonocytes inducing energy deficiency in the cell and increasing apoptosis and proliferation. Additionally, ammonia and other protein-derived metabolites such as B-SOFA present in the lumen can impair barrier function and promote pro-inflammatory signalling expression in the colonic mucosa, which negatively influence the expression of monocarboxylate transporter 1 (MCT1) (Villodre et al. *Brit. J. Nutr.* 113, 610 (2015)). MCT1 is stimulated by butyrate leading to increase butyrate uptake by colonocytes. The inhibition of MCT1 by high concentration of protein-derived metabolites in the intestine can impair the protective effect of butyrate on the colon epithelium and lead to pro-inflammatory conditions in the colon. High ammonia levels have been shown to increase inflammatory lesions in rats, which are established precursors in animal models and humans to the development of colon rectal cancer (Pieper et al. *Anim. Health Res.* Rev. 17, 137 (2016)).

Normally, gut-derived ammonia is taken up by the liver and consumed in the urea cycle and passes out of the body in urine. However, altered intestinal permeability can increase the delivery of compounds such as ammonia to the liver causing liver saturation and making the liver inefficient in processing ammonia. The ammonia is then returned to the blood for circulation. High concentration of ammonia in the blood can cause damage to the liver and affect the central nervous system such as impairing intracerebral synthesis of serotonin and dopamine and producing abnormal neurotransmitters such as octopamine. Elevated levels of detrimental proteolytic metabolites such as ammonia in plasma in patients with acute liver failure and chronic liver disease have been found, and higher concentration of faecal ammonia has been reported in children with autism spectrum disorders (43 mmol/g faeces) compared with control children (32 mmol/g faeces) (Wang et al. *Dig. Dis. Sci.* 57, 2096 (2012)).

An important determinant for the degree of proteolytic versus saccharolytic fermentation is the nutrient availability and in particular the ratio of available carbohydrate to nitrogen. The production of protein degradation products can generally be reduced by increasing the amount of fermentable carbohydrate reaching the colon (Vernazza et al., in: *Prebiotics: Development and Application* (Gibson et al. eds.), Chapter 1, John Wiley & Sons, 2006). Hence, selective stimulation of specific saccharolytic intestinal bacteria to promote their growth and metabolic activity, and inhibit the growth of unfavourable bacteria such as proteolytic bacteria could be a helpful approach in shifting the bacterial metabolism from a proteolytic to a saccharolytic metabolism. This leads to reduction of detrimental proteolytic metabolites such as ammonium and branched SOFA, and an increase of beneficial metabolites such as SOFA.

Human milk oligosaccharides (HMOs) are a heterogeneous mixture of soluble glycans found in human milk. They are the third most abundant solid component after lactose and lipids in human milk and are present in concentrations of 5-25 g/l (Bode, in: *Handbook of dietary and nutritional aspects of human breast milk* (Zibadi et al. eds.), 515-31, Wageningen Academic Publishers (2013)). HMOs are resistant to enzymatic hydrolysis in the small intestine and are thus largely undigested and unabsorbed. The majority of HMOs that reach the colon serve as substrates to shape the gut ecosystem by selectively stimulating the growth of specific saccharolytic bacteria. HMOs are believed to substantially modulate the infant gut microbiota and play a decisive role in the differences in the microbiota of formula-fed and breast-fed infants. These differences include the predominance of bifidobacteria in the gut of breast-fed infants compared to a more diverse gut microbiota in formula-fed infants. This is viewed as beneficial for the infant because strains of *Bifidobacterium* species are believed to have a positive effect on gut health (Chichlowski et al. *J. Pediatr. Gastroenterol. Nutr.* 55, 321 (2012)). However, it is not known if HMOs can decrease proteolytic bacteria in the adult human intestine.

There is a need, therefore, for means, preferably orally or enterally administered means, more preferably dietetic means, for effectively changing the microbiota ecosystem leading to a decrease in the concentration of detrimental proteolytic metabolites such as ammonia and branched short chain fatty acids in the gastro-intestinal tracts of humans.

SUMMARY OF THE INVENTION

A first aspect of this invention relates to one or more human milk oligosaccharides (HMOs), advantageously a neutral HMO, for use in decreasing the concentration of detrimental proteolytic metabolites such as ammonia and branched short chain fatty acids in the gastro-intestinal tract of a human.

A second aspect of the invention is a synthetic composition comprising one or more human milk oligosaccharides (HMOs), advantageously a neutral human milk oligosaccharide, for use in decreasing detrimental proteolytic metabolites such as ammonia and branched short chain fatty acids, in the gastro-intestinal tract of a human.

The synthetic composition can be a nutritional or pharmaceutical composition.

A third aspect of this invention is a method for decreasing detrimental proteolytic metabolites such as ammonia and branched short chain fatty acids in the gastro-intestinal tract of a human, the method comprising orally or enterally administering to the human an effective amount of a human milk oligosaccharide, advantageously a neutral HMO.

A fourth aspect of this invention is a method for the prophylaxis or treatment of a human having a brain-gut disorder, the method comprising orally or enterally administering, to the human, an amount of one or more human milk oligosaccharides, advantageously neutral HMOs, effective to decrease detrimental proteolytic metabolites such as ammonia and branched short chain fatty acids in the gastro-intestinal tract of the human. The brain-gut disorder may be autism, stress, anxiety or depressive disorder.

A fifth aspect of this invention is a method for the prophylaxis or treatment of a human at risk of or suffering from colon cancer and/or liver damage, the method comprising orally or enterally administering to the human one or more human milk oligosaccharides, advantageously a neutral HMO, or a synthetic composition containing a HMO, advantageously a neutral HMO, for decreasing detrimental proteolytic metabolites such as ammonia and branched short chain fatty acids in the gastro-intestinal tract of the human.

A sixth aspect of the invention is a use of
one or more human milk oligosaccharides (HMOs), advantageously a neutral HMO,
a synthetic composition comprising one or more human milk oligosaccharides (HMOs), advantageously a neutral HMO, or
a pack comprising at least 7 individual daily doses of an effective amount of one or more human milk oligosaccharides (HMOs), advantageously a neutral HMO,
in the dietary management of a human
having an increased concentration of detrimental proteolytic metabolites, such as ammonia and branched short chain fatty acids, in the gastro-intestinal tract,
having a disease associated with an increased concentration of detrimental proteolytic metabolites, such as ammonia and branched short chain fatty acids, in the gastro-intestinal tract,
having a brain-gut disorder associated with elevated concentrations of ammonia in the intestine, and/or
being at risk of or suffering from colon cancer and/or liver damage.

In the third to sixth aspect, preferably, the HMO(s) is/are administered for at least 14 days, more preferably at least 21 days.

Preferably the concentration of ammonia in the colon is decreased by at least 10% as compared to its concentration prior to HMO administration; more preferably by at least 20%. The concentration of branched short chain fatty acids in the colon is preferably decreased by at least 10% as compared to their concentration prior to HMO administration, more preferably by at least 20%. Further, the concentration of butyrate in the proximal colon is preferably increased by at least 50%; more preferably by at least 100%, after 14 days.

A seventh aspect of the invention relates to a pack for use in decreasing the concentration of detrimental proteolytic metabolites such as ammonia and branched short chain fatty acids in the gastro-intestinal tract of a human, the pack comprising at least 7 individual daily doses of an effective amount of one or more human milk oligosaccharides, advantageously a neutral HMO. Preferably, each dose contains about 1 g to about 20 g of the human milk oligosaccharide, more preferably about 2 g to about 10 g, for example about 3 g to about 7.5 g. Preferably, the pack comprises at least 14 individual daily doses; more preferably at least 21 daily doses; for example at least 28 daily doses. The pack can include instructions for use.

In all aspects disclosed above, preferably, the neutral HMO is a fucosylated neutral HMO, such as 2'-FL, 3-FL or DFL, or a mixture thereof, a non-fucosylated neutral HMO, such as LNnT or LNT, or a mixture thereof, especially a mixture of a fucosylated and a non-fucosylated neutral HMO.

BRIEF DESCRIPTION OF THE FIGURES

FIG. 1 illustrates the effect of 2'-FL on branched SOFA and ammonia production (mg/l) in the proximal (PC) and distal (DC) colon reactor. Samples were taken during two control weeks (C), three treatment weeks (T) and two washout weeks (W), for metabolic analysis.

DETAILED DESCRIPTION OF THE INVENTION

It has now been surprisingly found that administration of human milk oligosaccharides (HMOs) to humans decreases the concentration of detrimental proteolytic metabolites such as ammonia and branched chain fatty acids in the gastro-intestinal tract the human. The human milk oligosaccharides, by oral or enteral ingestion, dynamically modulate the intestinal microbiota by preferentially promoting the growth of bifidobacteria of the *B. adolescentis* phylogenetic group, especially *Bifidobacterium adolescentis* and/or *Bifidobacterium pseudocatenulatum*, and, after about 14 days, *Bifidobacterium longum* and/or *Bifidobacterium bifidum*. Surprisingly, this correlates with the substantial reduction of the concentration of ammonia and branched short chain fatty acids in the proximal and distal colon. Further, in about 14 days, the production of butyrate in the gastro-intestinal tract increases. Accordingly, a more beneficial intestinal microbial community and intestinal environment can be shaped and maintained, and the production of compounds potentially harmful to human health, such as branched short chain fatty acids (B-SOFA), ammonia, etc. strongly reduced.

Herein, the following terms have the following meanings:

"Human" may in different embodiments relate to a child, a teenager, an adult or an elderly person.

"Human milk oligosaccharide" or "HMO" means a complex carbohydrate found in human breast milk (Urashima et al.: Milk Oligosaccharides. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH) .Examples of neutral fucosylated HMOs include 2'-fucosyl-lactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH 11) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition of the invention may be, but preferably is not, identical with a naturally occurring composition. The synthetic composition typically comprises one or more compounds, advantageously HMOs, that are capable of preferentially increasing the abundance of bifidobacteria in the microbiota of the gastro-intestinal tract. In some embodiments, the synthetic composition may comprise one or more compounds or components other than HMOs that may have an effect on bifidobacteria of a human subject's microbiota in vivo, e.g. non-digestible oligosaccharides or prebiotics. Also in some embodiments, the synthetic compositions may comprise one or more nutritionally or pharmaceutically active components which do not affect adversely the efficacy of the above-mentioned compounds.

Some non-limiting embodiments of a synthetic composition of the invention are also described below.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" preferably means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

"Oral administration" preferably means any conventional form for the delivery of a composition to a human through the mouth. Accordingly, oral administration is a form of enteral administration.

"Effective amount" preferably means an amount of a composition that provides an HMO in a sufficient amount to render a desired treatment outcome in a human. An effective amount can be administered in one or more doses to achieve the desired treatment outcome.

"Relative abundance of a *Bifidobacterium longum* and/or *Bifidobacterium bifidum*" means the abundance of a *Bifidobacterium longum* and/or *Bifidobacterium bifidum* relative to other bifidobacteria in the microbiota of the gastro-intestinal tract of humans.

"Relative growth of a *Bifidobacterium longum* and/or *Bifidobacterium bifidum*" means the growth of a *Bifidobacterium longum* and/or *Bifidobacterium bifidum* relative to other bifidobacteria in the microbiota in the gastro-intestinal tract of humans.

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. Appl. Environ. *Microbiol.* 79, 336 (2013), Bottacini et al. *Microbial Cell Fact.* 13:S4 (2014)). Preferably, a *Bifidobacterium* of the *B. adolescentis* phylogenetic group is *Bifidobacterium adolescentis* and/or *Bifidobacterium pseudocatenulatum*.

"Relative abundance of a *Bifidobacterium* of the *B. adolescentis* phylogenetic group" means the abundance of a *Bifidobacterium* of the *B. adolescentis* phylogenetic group relative to other bifidobacteria in the microbiota of the gastro-intestinal tract of humans.

"Relative abundance of *B. adolescentis* and/or *B. pseudocatenulatum*" means the abundance of *B. adolescentis* and/or *B. pseudocatenulatum* relative to other bifidobacteria in the microbiota of the gastro-intestinal tract of humans.

"Relative growth of a *Bifidobacterium* of the *B. adolescentis* phylogenetic group" means the growth of a *Bifidobacterium* of the *B. adolescentis* phylogenetic group relative to other bifidobacteria in the microbiota in the gastro-intestinal tract of humans.

"Relative growth of *B. adolescentis* and/or *B. pseudocatenulatum*" means the growth of *B. adolescentis* and/or *B.*

*pseudocatenulatum* relative to other bifidobacteria in the microbiota in the gastro-intestinal tract of humans.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

The term "dietary management" means exclusive or partial feeding of patients who, because of a disease, disorder or medical condition they are suffering from:
   either have a limited, impaired or disturbed capacity to take, digest, absorb, metabolise or excrete ordinary food or certain nutrients contained therein, or metabolites, or
   have other medically-determined nutrient requirements
   (see: Commission Notice on the classification of Food for Special Medical Purposes of the European Commission, *Official Journal of the European Union C* 401, 25, Nov. 2017, p. 10-11).

In accordance with this invention, it has been discovered that an HMO, preferably a neutral HMO, can reduce the concentration of detrimental proteolytic metabolites in the colon. Further, the HMO can stimulate the production of butyrate in the gastro-intestinal tract of a human, when administered to the human for about 14 days. Accordingly, an HMO can be used for treating, reducing or preventing the formation of elevated concentrations of detrimental proteolytic metabolites in the gastrointestinal tract of humans; for example humans having gut-brain disorders and extra-intestinal diseases such as autism, colon cancer and liver damage.

Accordingly, the first aspect of the invention relates to an HMO, advantageously a neutral HMO, for use in decreasing the concentration of detrimental proteolytic metabolites such as ammonia and branched short chain fatty acids in the gastro-intestinal tract of a human.

The neutral HMO is in one embodiment one or more fucosylated HMOs; in another embodiment, the HMO is one or more non-fucosylated HMOs. In one embodiment, the neutral HMO is a mixture neutral HMOs, preferably a mixture comprising or consisting of a fucosylated and a non-fucosylated neutral HMO. Particularly, the mixture contains or consists of one or more fucosylated neutral HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, preferably, at least 2'-FL, and a non-fucosylated neutral HMO selected from the list consisting of LNT, LNnT, LNH, LNnH, pLNH and pLNnH, e.g. LNnT. In some preferred embodiment, the mixture contains or consists of a fucosylated neutral HMO selected from the list consisting of 2'-FL, 3-FL and DFL, and a non-fucosylated neutral HMO selected from the list consisting of LNT and LNnT, advantageously the mixture comprises or consists of i) 2'-FL and/or DFL and ii) LNnT and/or LNT (meaning that the mixture comprises or consists of at least one of 2'-FL and DFL, and at least one of LNnT and LNT, for example a mixture comprising or consisting of 2'-FL and LNnT). The mixture can also be that containing or consisting of 2'-FL and DFL. In other embodiments, the HMO includes acidic HMOs such as 3'-SL and 6'-SL.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 201 2/1 5591 6 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2011/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The second aspect of this invention is a synthetic composition comprising an HMO, preferably a neutral HMO or a mixture of neutral HMOs, even more preferably a mixture of a fucosylated and a non-fucosylated neutral HMOs as disclosed above in the first aspect, for use in decreasing the concentration of detrimental proteolytic metabolites such as ammonia and branched short chain fatty acids in the gastro-intestinal tract of a human.

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a human can be determined in a conventional manner, based upon factors such immune status, body weight and age. In some cases, the dosage will be at a concentration similar to that found for the HMO, advantageously a neutral HMO, in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition.

Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for humans having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. B. animalis subsp. lactis BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a human via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition, preferably the nutritional composition, can also be in a unit dosage form such as a capsule, tablet or sachet/stick pack. For example, the synthetic composition, preferably the nutritional composition, can be in a tablet or powder form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet/stick pack form, can also include various nutrients including macronutrients.

The HMO or synthetic composition can be presented in the form of a pack comprising at least 7 individual daily doses of an effective amount of the human milk oligosaccharide. The daily doses are preferably in sachet/stick pack form but may be in any suitable form. Each dose preferably contains about 1 g to about 20 g of the human milk oligosaccharide, more preferably about 2 g to about 10 g, for example about 3 g to about 7.5 g. Preferably, the pack comprises at least 14 daily doses; more preferably at least 21 daily doses. Most suitable packs contain sufficient for 4 weeks or a full month. The pack can include instructions for use.

The HMO or the nutritional composition disclosed above is suitable for the dietary management of a human having an increased concentration of detrimental proteolytic metabolites such as ammonia and branched short chain fatty acids in the gastro-intestinal tract, having a disease associated with an increased concentration of detrimental proteolytic metabolites such as ammonia and branched short chain fatty acids in the gastro-intestinal tract, having a brain-gut disorder associated with elevated concentrations of ammonia in the intestine, and/or being at risk of or suffering from colon cancer and/or liver damage.

A first target group of this invention includes healthy humans. Their ingestion of one or more HMOs, preferably a mixture of neutral HMOs, even more preferably a mixture of a fucosylated and a non-fucosylated neutral HMO, will reduce the concentration of detrimental proteolytic metabolites in the gastrointestinal tract. Further, when administered for a period of at least about 14 days will stimulate the production of butyrate in the gastro-intestinal tract of the healthy human. This will improve the gastrointestinal health of the human.

A second target group includes humans having a condition or disease associated with elevated levels of detrimental proteolytic metabolites such as humans having a gut-brain disorder, colon cancer and/or liver damage. Their ingestion of one or more HMOs, preferably a mixture of neutral HMOs, even more preferably a mixture of a fucosylated and a non-fucosylated neutral HMO, will reduce the concentration of detrimental proteolytic metabolites in the gastrointestinal tract. Further, when administered for a period of at least about 14 days, it will stimulate the production of butyrate in the gastro-intestinal tract of the healthy human. This will improve the gastrointestinal health of the human.

A third aspect of this invention is a method for decreasing detrimental proteolytic metabolites such as ammonia and branched short chain fatty acids in the gastro-intestinal tract of a human, the method comprising orally or enterally administering to the human an effective amount of a human milk oligosaccharide, advantageously a neutral HMO.

Preferably, the method according to the third aspect is a dietary management.

A fourth aspect of this invention is a method for the prophylaxis, treatment or dietary management of a human having a brain-gut disorder, the method comprising orally or enterally administering to the human, an amount of one or more human milk oligosaccharides, advantageously neutral HMOs, effective to decrease detrimental proteolytic metabolites such as ammonia and branched short chain fatty acids in the gastro-intestinal tract of the human. The brain-gut disorder may be autism, stress, anxiety and depressive disorder.

A fifth aspect of this invention is a method for the prophylaxis, treatment or dietary management of a human at risk of or suffering from colon cancer and/or liver damage, the method comprising orally or enterally administering to the human one or more human milk oligosaccharides, advantageously a neutral HMO, or a synthetic composition containing a HMO, advantageously a neutral HMO, for decreasing detrimental proteolytic metabolites such as ammonia and branched short chain fatty acids in the gastro-intestinal tract of the human. To additionally stimulate the production of butyrate in the gastro-intestinal tract of the human, the method comprises enterally, preferably orally, administering to the human:

(a) in a first step for a period of about 14 days:
a first amount of one or more HMOs, or
a first amount of synthetic composition comprising an effective amount one or more HMOs, to increase the level of butyrate in the gastro-intestinal tract of the human to the level up to 100% or more, such as 200%-500% higher, compared to the butyrate level before the initiation of administration, and
(b) in a second step for an additional period:
a second amount of one or more HMOs, or
a second amount of a synthetic composition comprising an effective amount one or more HMOs,
to maintain the level of butyrate production in the gastro-intestinal tract of the human achieved after the 14-day administration of the first amount of the HMO or the HMO composition.

A sixth aspect of the invention is a use of
one or more human milk oligosaccharides (HMOs), advantageously a neutral HMO,
a synthetic composition comprising one or more human milk oligosaccharides (HMOs), advantageously a neutral HMO, or
a pack comprising at least 7 individual daily doses of an effective amount of one or more human milk oligosaccharides (HMOs), advantageously a neutral HMO,
in the dietary management of a human
having an increased concentration of detrimental proteolytic metabolites such as ammonia and branched short chain fatty acids in the gastro-intestinal tract,
having a disease associated with an increased concentration of detrimental proteolytic metabolites such as ammonia and branched short chain fatty acids in the gastro-intestinal tract,
having a brain-gut disorder associated with elevated concentrations of ammonia in the intestine, and/or
being at risk of or suffering from colon cancer and/or liver damage.

In the third to fifth aspects of therapeutic and prophylactic treatment or dietary management, or in the sixth aspect of the invention, the HMO is advantageously a neutral HMO as described above. The HMO can also include acid HMOs such as 3'-SL and 6'-SL.

For reducing detrimental proteolytic metabolites in the gastro-intestinal tract of a human, the amount of HMO(s) required to be administered will vary depending upon factors such as the risk and severity of the condition or disease, age, the form of the composition, and other medications being administered. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, body weight and/or condition, the severity of the of condition or the disease being treated or prevented, other ailments and/or diseases, the incidence and/or severity of side effects and the manner of administration. Appropriate dose ranges may be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g or 1 g to 3 g per day).

Whilst the invention has been described with reference to a preferred embodiment, it is understood that various modifications are possible within the scope of the invention.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 4 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 4 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.

Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

After 2 weeks, each participant has a visit with the medical team. Faecal samples and blood samples are collected. The faecal samples are stored at −80° C. until analysis. Equipment for new samples are distributed. Subjects are reminded not to change their usual diet during the study.

After 4 weeks, each participant has an exit visit with the medical team. Faecal samples and blood samples are collected. The faecal samples are stored at −80° C. until analysis.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-B10). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. Nucleic Acids Res. 41, el (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013)) is used for bioinformatical analysis of the sequence data.

To assess the *Bifidobacterium* community, ITS profiling of DNA samples is performed.

The results from the profiling of the *Bifidobacterium* community shows that, for the first 2 weeks, the abundance of *B. adolescentis* increases when consuming a single HMO, where the abundance of *B. psedocatenulatum* increases when consuming a mix of two HMOs. Both *B. adolescentis* and *B. psedocatenulatum* are members of the *B. adolescentis* phylogenetic group. At 4 weeks, the abundance of members of the *B. adolescentis* phylogenetic group reduce while the abundance of *Bifidobacterium longum* and/or *Bifidobacterium bifidum* increase. It can be seen that oral ingestion of the HMOs for more than 14 days clearly increases the abundance of *Bifidobacterium longum* and/or *Bifidobacterium bifidum* in the microbiota of healthy adults, as well as their relative abundance compared to the totality of other *Bifidobacterium* species. Further the concentration of proteolytic metabolites decreases.

Example 2

The impact of the HMOs on microbiota and bacterial metabolites was investigated in the M-SHIME® (M-TripleSHIME®) in vitro gastrointestinal model (Prodigest). The typical reactor setup of the M-TripleSHIME® consisted of a succession of four reactors simulating the different parts of the human gastrointestinal tract. The first two reactors were of the fill-and-draw principle to simulate different steps in food uptake and digestion, with peristaltic pumps adding a defined amount of SHIME feed (140 mL 3×/day) and pancreatic and bile liquid (60 ml 3×/day), respectively, to the stomach and small intestine compartment and emptying the respective reactors after specified intervals. The last two compartments were continuously stirred reactors with constant volume and pH control. The retention time and pH of the different vessels were chosen to resemble in vivo conditions in the different parts of the colon. The proximal colon was set to pH 5.4-5.6 and retention time=12 h, and the distal colon was set to pH 6.0-6.5 and retention time=20 h. 2'-FL, LNnT or Mix (2'-FL:LNnT in 4:1 weight ratio) was added to the SHIME feed in a concentration that equalled 10 gram per day. Upon inoculation with faecal microbiota, these reactors simulated the ascending and descending colon. After a two-week adaptation of the microbial communities in the different regions of the colon, a representative microbial community was established in the colon compartments, which differed both in composition and functionality in the different colon regions.

Further, porcine mucin capsules were included in the reactors simulating the colon to take into account the colonisation of the mucous layer. Thus the M-SHIME® permitted culturing both the luminal and mucous-associated microbial community over periods of several weeks.

The M-TripleSHIME® was run in four stages:
1. Stabilisation: After inoculation of the reactors with a fresh faecal sample taken from a healthy adult, a two-week stabilisation period allowed the microbial community to differentiate in the different reactors depending on the local environmental conditions. During this period the basic nutritional matrix was provided to support the maximum diversity of the gut microbiota originally present in the faecal inoculum.
2. Control: During this two-week period, a standard nutrient matrix was dosed into the model for a period of 14 days. The baseline microbial community composition and activity in the different reactors was determined by analysis of samples and was used as a reference.
3. Treatment: The SHIME system was operated under normal conditions for 3 weeks, but with the standard nutrient matrix supplemented with the HMOs. The HMOs tested were 2'-FL, LNnT and a 4:1 mix of 2'-FL and LNnT.
4. Washout: During this two-week period, the SHIME system was again run with the standard nutrient matrix only.

Sample of the liquids in each reactor were collected regularly (three times in a week, on day 1, day 3 and day 5) and were analysed for microbial metabolites and the composition of the resident microbial community. In particular, the bifidobacteria composition was analysed using ITS profiling.

The results from the fermentation system showed that HMOs impacted the base-acid consumption meaning that HMOs were fermented both in the proximal colon and, to a lesser extent, the distal colon. The profiling of the Bifidobacterium community showed that, for the first 2 weeks, the abundance of *B. adolescentis* increased when consuming HMOs. However, by week 3, the relative abundance of members of the *B. adolescentis* phylogenetic group reduced while the abundance and relative abundance of *Bifidobacterium longum* and/or *Bifidobacterium bifidum* increased. Additionally, the relative abundance of proteolytic bacteria was decreased and butyrate-producing bacteria within the Lachnospiracea family were increased.

FIG. 1 shows the effect of 2'-FL on branched SOFA and ammonia production (mg/l) in the proximal (PC) and distal (DC) colon reactor. The values plotted are means of the three weekly samples. The results of the tests concerning LNnT or the mixture of 2'-FL:LNnT are similar.

The bacterial metabolite analysis showed that HMO treatment induced an immediate increase in total SOFA production in both colon regions, mainly due to increase in the production of acetate and propionate. During the third week of HMO treatment, butyrate was increased. Additionally, the analysis showed that ammonia and branched short chain fatty acids was decreased during treatment with the HMOs in both the proximal and distal colon.

It can be seen that feeding the M-SHIME with HMOs shifts the bacterial community leading to a beneficial shift in the bacterial metabolism from a proteolytic to a saccharolytic metabolism.

The invention claimed is:

1. A method comprising:
    selecting a non-infant human with elevated concentrations of detrimental proteolytic metabolites selected from ammonia, branched short chain fatty acids, and combinations thereof;
    selecting an effective amount of a composition consisting essentially of one or more synthetic human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of a non-infant human;
    shifting the gastrointestinal microbiota of the non-infant human away from a proteolytic metabolism toward a saccharolytic metabolism by increasing the relative abundance of *Bifidobacterium adolescentis* and causing a delayed increase of butyrate in colon of the non-infant human by administering the effective amount of the chosen HMOs to the non-infant human, wherein during an initial treatment phase, the effective amount is a daily dosage for non-infants of from about 3 g to about 10 g per day; and
    decreasing the elevated concentrations of the detrimental proteolytic metabolites in the gastrointestinal tract of the non-infant human.

2. The method of claim 1, further comprising increasing the relative abundance of *Bifidobacterium longum* and/or *Bifidobacterium bifidum* concurrently with the delayed increase in colonic butyrate by administering the effective amount of the chosen HMOs to the non-infant human.

3. The method of claim 1, wherein the condition associated with an elevated concentration of the detrimental proteolytic metabolites is a gut-brain disorder.

4. The method of claim 3, wherein the gut-brain disorder is selected from stress, anxiety, and combinations thereof.

5. The method of claim 1, wherein during a maintenance phase following the initial treatment phase, the daily dosage for non-infants is reduced from about 3 g to 10 g per day to about 1 g to 3 g per day.

6. The method of claim 1, wherein the one or more synthetic HMOs consists essentially of a mixture of one or more neutral fucosylated HMOs selected from 2'-FL, 3-FL, DFL, and LNFP-I and one or more neutral non-fucosylated HMOs selected from LNT and LNnT.

7. The method of claim 1, wherein composition consists essentially of a mixture of two or more HMOs selected from 2'-FL, DFL, 3-FL, LNT, LNnT.

8. The method of claim 7, wherein the composition consists essentially of 2'-FL, LNnT, or the combination thereof.

9. A method comprising:
    selecting a non-infant human with elevated concentrations of gut-derived ammonia associated with liver dysfunction;
    selecting an effective amount of a composition consisting essentially of one or more synthetic human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of a non-infant human; and
    reducing the elevated concentrations of gut-derived ammonia by increasing the relative abundance of *Bifidobacterium adolescentis* and causing a delayed increase of butyrate in colon of the non-infant human by administering the effective amount of the chosen HMOs to the non-infant human, wherein during an initial treatment phase, the effective amount is a daily dosage for non-infants of from about 3 g to about 10 g per day.

10. The method of claim 9, wherein the liver dysfunction is select from acute liver failure and chronic liver disease.

11. The method of claim 10, wherein the concentration of ammonia or branched short chain fatty acids in the colon is decreased by at least 10% as compared to the concentration prior to the administration of the selected one or more HMOs.

12. The method of claim 10, wherein the initial treatment phase is at least 14 days.

13. The method of claim 12, further comprising increasing the relative abundance of *Bifidobacterium longum* and/or *Bifidobacterium bifidum* concurrently with the delayed increase in colonic butyrate by administering the effective amount of the chosen HMOs to the non-infant human.

14. The method of claim 13, wherein the level of butyrate produced in the proximal colon is increased by at least 50% in response to the administration of the effective amount of the chosen one or more HMOs during the initial treatment phase.

15. A method comprising:
    selecting a non-infant human with elevated concentrations of gut-derived ammonia associated with development of colon cancer;
    selecting an effective amount of a composition consisting essentially of one or more synthetic human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of a non-infant human; and
    reducing the elevated concentrations of gut-derived ammonia by increasing the relative abundance of *Bifi-*

*dobacterium adolescentis* and causing a delayed increase of butyrate in colon of the non-infant human by administering the effective amount of the chosen HMOs to the non-infant human, wherein during an initial treatment phase, the effective amount is a daily dosage for non-infants of from about 3 g to about 10 g per day.

16. The method of claim 15, further comprising, causing a delayed increase inthe relative abundance of *Bifidobacterium longum* and/or *Bifidobacterium bifidum* by administering the effective amount of the chosen HMOs to the non-infant human.

17. The method of claim 15, wherein during a maintenance phase following the initial treatment phase, the daily dosage for non-infants is reduced from about 3 g to 10 g per day to about 1 g to 3 g per day.

18. The method of claim 15, wherein the composition consists essentially of neutral HMOs chosen from 2'-FL, DFL, LNnT, LNT, and combinations thereof.

* * * * *